US012714300B2

(12) United States Patent
Neal et al.

(10) Patent No.: US 12,714,300 B2
(45) Date of Patent: Aug. 25, 2026

(54) METHODS OF AUTOMATED DETERMINATION OF PARAMETERS FOR VISION CORRECTION

(71) Applicant: Wavefront Dynamics, Inc., Albuquerque, NM (US)

(72) Inventors: Daniel R. Neal, Tijeras, NM (US); Xifeng Xiao, Albuquerque, NM (US); Jeff Kolberg, Laguna Beach, CA (US); Ron Rammage, Tijeras, NM (US)

(73) Assignee: WAVEFRONT DYNAMICS, INC., Albuquerque, NM (US)

( * ) Notice: Subject to any disclaimer, the term of this patent is extended or adjusted under 35 U.S.C. 154(b) by 947 days.

(21) Appl. No.: 17/891,083

(22) Filed: Aug. 18, 2022

(65) Prior Publication Data

US 2023/0148857 A1 May 18, 2023

Related U.S. Application Data

(63) Continuation-in-part of application No. 17/183,327, filed on Feb. 23, 2021, now Pat. No. 12,220,170.

(51) Int. Cl.
*A61B 3/00* (2006.01)
*G16H 50/20* (2018.01)

(52) U.S. Cl.
CPC ........... *A61B 3/0025* (2013.01); *G16H 50/20* (2018.01)

(58) Field of Classification Search
CPC ....... A61B 3/1015; A61B 3/103; A61B 3/107; A61B 3/1005; A61B 3/0025; A61B 3/113; A61B 3/028; A61B 3/036; A61B 3/04; A61B 3/09; A61B 3/16; G02C 2202/22; G02C 7/04; G02C 7/047; G02C 7/022

See application file for complete search history.

(56) References Cited

U.S. PATENT DOCUMENTS

| | | | | |
|---|---|---|---|---|
| 7,780,293 | B2 | 8/2010 | Adino | |
| 8,623,081 | B2 | 1/2014 | Canovas | |
| 10,500,092 | B2 | 12/2019 | Raymond | |
| 10,506,920 | B2 | 12/2019 | Hasser | |
| 10,506,923 | B2 * | 12/2019 | Neal | G02B 27/286 |
| 10,583,039 | B2 | 3/2020 | Raymond | |
| 10,722,180 | B2 | 7/2020 | Zhang | |
| 11,013,405 | B1 | 5/2021 | Karpecki | |

(Continued)

FOREIGN PATENT DOCUMENTS

| | | | | |
|---|---|---|---|---|
| JP | 2018528543 | * | 9/2016 | G06V 10/993 |

OTHER PUBLICATIONS

Wu X, Huang Y, Liu Z, et al. "Universal artificial intelligence platform for collaborative management of cataracts" Br J Ophthalmol. 2019;103(11):1553-1560).

(Continued)

*Primary Examiner* — Brandi N Thomas
(74) *Attorney, Agent, or Firm* — Quinn IP Law

(57) ABSTRACT

A method for optimizing an ophthalmic treatment, comprising: measuring a patient's eye with an ophthalmic measurement instrument, fabricating a trial correction lens and testing it on the patient's eye, determining a score or success criteria for the trial correction, using the score or success criteria to provide training information to a machine-learning algorithm, and using the machine-learning algorithm to determine an optimal ophthalmic correction.

19 Claims, 4 Drawing Sheets

(56) References Cited

U.S. PATENT DOCUMENTS

| | | | | |
|---|---|---|---|---|
| 11,051,688 | B2 | 7/2021 | Neal | |
| 11,058,295 | B2 | 7/2021 | Okazaki | |
| 2013/0135586 | A1 * | 5/2013 | Lai ...................... | A61B 3/1015<br>351/216 |

OTHER PUBLICATIONS

Souza MB et al, "Machine learning classifiers in keratoconus detection", Clinics 2010;65(12):1223-1228.
Chalmers R, et al. "Adverse event rates in the retrospective cohort study of safety of paediatric soft contact lens wear: the ReCSS Study", Ophthalmic Physiol Opt. 2020;doi:10.1111/opo.12753.
A. Lavric et al.: Detecting Keratoconus From Corneal Imaging Data Using Machine Learning, IEEE Access, Aug. 12. 2020., vol. 8, 2020 pp. 149113-149121.
Kin Wei, Larry Thibos "Design and validation of a scanning Shack Hartmann aberrometer for measurements over a wide field of view," Optics Express, Jan. 18, 2010, vol. 18, No. 2, , p. 1134-1143.
Padmaja Sankaridurg, "Contact lenses to slow progression of myopia—Invited Revew, " Clinical and Experimental Optometry, 2017, vol. 100, pp. 432-437.
Torres Netto EA,Al-Otaibi WM, Hafezi NL, et al. "Prevalance of Keratoconus in paediatric patients in Riyadh, Saudi Arabia", Br J Ophthalmol, 2018;102:1436-1441.

* cited by examiner

METHODS OF AUTOMATED DETERMINATION OF PARAMETERS FOR VISION CORRECTION

CROSS-REFERENCE TO RELATED APPLICATIONS

This application claims the benefit of commonly-owned U.S. Provisional patent application Ser. No. 63/230,657 filed Aug. 6, 2021, which is incorporated herein by reference. This application is also a continuation-in-part of U.S. patent application Ser. No. 17/183,327, "Improved Aberrometer and Methods for Contact Lens Fitting and Customization", filed Feb. 23, 2021, which is incorporated herein by reference in its entirety, and which claims the benefit of said previous application.

TECHNICAL FIELD

The present invention relates to a method of using artificial intelligence (AI) to optimize an ophthalmic correction using contact lens or spectacles.

BACKGROUND

Design and fitting of ophthalmic correction is a combination of art and science. While it has been possible to measure various parameters of the eye for some time, there is still an art to the selection of the correct fit for contact lenses, or the correct refraction for either spectacles or contacts. This is complicated significantly if the patient has one of several eye diseases, such as: keratoconus or pellucid marginal degeneration. While there are good "rule-of-thumb" systems for determining the parameters needed for ophthalmic correction, these often do not work properly for the more unusual eyes. For example, for a strong keratoconic person, it can be difficult to find a consistent refraction for even the basic SCA parameters (sphere, cylinder, and axis).

Artificial intelligence (AI) techniques have advanced significantly over the last several years. Major advancements over the last quarter century have led innovations in speech recognition, natural language processing, medical diagnosis, and many other applications. In laser refractive surgery or cataract surgery the use of a nomogram to adjust the treatment is relatively common, and there are several products and services based on this concept (e.g., SurgiVision Consultants). Several inventors have developed various methods for taking measurement information and transforming that information into parameters for treatment. These may include linear methods (U.S. Ser. No. 10/500,092, U.S. Pat. Nos. 8,623,081, 7,780,293, U.S. Ser. No. 11/013,405, U.S. Ser. No. 11/051,688, U.S. Ser. No. 11/058,295) or systems using some form of machine learning (ML) or AI (U.S. Ser. No. 10/506,923, U.S. Ser. No. 10/583,039, U.S. Ser. No. 10/722,180). Increasingly AI techniques have been used for cataract planning (e.g., Wu X, Huang Y, Liu Z, et al. "Universal artificial intelligence platform for collaborative management of cataracts" *Br J Ophthalmol.* 2019; 103(11):1553-1560) and detection of various ocular conditions (Zhang K, Liu X, Liu F, et al. "An interpretable and expandable deep learning diagnostic system for multiple ocular diseases: qualitative study," *J Med Internet Research.* 2018; 20(11):e11144, Xiao W, Huang X, Wang J H, et al. "Screening and identifying hepatobiliary diseases through deep learning using ocular images: a prospective, multicentre study," *Lancet Digit Health.* 2021; 3(2):e88-e97).

However, like all computerized analysis of data, the results of these computations depend strongly on the quality of the input data. If the input data is not representative of the subject population, or does not include parameters that are sensitive to the process, then even the best AI algorithm would not be capable of determining an optimal ophthalmic correction. For example, it is unlikely that corneal topography data could be used to predict macular degeneration. While the corneal topography data contains information about the optical image quality, it has no data on the function of the retina. Thus, it is important the input data contain information that affects the desired output.

While there are many potential measurements of an eye that can be used for ophthalmic treatment planning, these measurements may depend on the state of the eye during measurements. For example, it has been difficult to use auto-refractor data directly in correction design because it may depend on instrument accommodation, pupil size or other factors. While it is often used as a starting point for manifest refraction, it is rarely used for final refraction selection. Similarly, it is possible to use the k-values to provide an assessment of the base-curve for a contact lens, but these describe only a small region on the cornea, which is not the same as the len's landing zone. Some overall parameters, such as lens sag, may be determined by the k-values and iris diameter, but these algorithms don't work as well for diseased eyes, and hence the result is a trial-and-error methodology.

AI is extremely good at sorting through a large amount of data and determining optimum parameters, as long as it has good input data and an adequate scoring system. It often relies on large data sets to provide adequate training. But if the eye is in the wrong state (or a random state) due to accommodation, tear film, or fixation, then it will reduce the predictability of the results.

It is therefore desirable to couple AI techniques with a well-designed ophthalmic instrument that controls the state of measurement of the eye and measures all the relevant phenomena. In particular, Supervised Machine Learning (SLA) Algorithms are well suited to problems where good input data can be coupled with known treatment decisions by a human expert to allow the algorithm to predict the expert's choice of an optimal treatment. Classification algorithms like: Logistic Regression, Decision Forest Classifiers, Artificial Neural Network Classifiers, and Support Vector Machine Classifiers are well suited to make predictions of optimal treatment modality, whereas Regression algorithms such as: Poisson, Linear, Bayesian Linear, Artificial Neural Network, or Decision Forest Regression algorithms are better suited to selecting the optimal parameters of a treatment within a given modality.

All references and patents described herein are hereby incorporated herein by reference in their entirety.

SUMMARY

The present invention relates to a method for optimizing an ophthalmic treatment, comprising: measuring a subject's eye with an ophthalmic measurement instrument, fabricating a trial correction contact lens and testing it on the subject, determining a score or success criteria for the trial correction, using the score or success criteria to provide training information to a machine-learning algorithm, and using the machine-learning algorithm to determine an optimal ophthalmic correction.

DETAILED DESCRIPTION OF THE INVENTION

Certain embodiments of an ophthalmic system can comprise (according to the present invention):

An ophthalmic device for measuring wavefront aberrations of a patient's eye;

An ophthalmic device for measuring cornea shape and elevation;

An ophthalmic device for measuring iris and pupil dimensions;

Means for dynamic capture of ocular measurements;

Means for collecting and storing information;

Means for measuring the eye in a controlled state of fixation (e.g., astigmatism, defocus);

Means for dynamically measuring the eye;

A method for generating correction prescriptions; and

A processor (local or cloud-based) for implementing a Machine Learning (ML) calculation.

The ophthalmic instruments described in co-pending U.S. application Ser. No. 17/183,327 includes all of the measurement capabilities described above. It is capable of dynamic measurements, and stores information in rapid sequences to local computer storage. This same instrument includes controls for the fixation target which allow for control of the target astigmatism and defocus (or fogging) in a controlled manner. This provides all the information needed for determining optimal refraction, aberration correction, tear film assessment, contact lens fitting, and spectacle fitting.

The information is stored locally, and then synchronized to a cloud-based storage system for further analysis.

The system can include an on-line part ordering or tracking system that tracks the orders placed by the eye care practitioner. This is correlated with the measurement data to provide scoring for the predictions. This is used to train the AI algorithm. Both success and failure data are important to improve the efficiency of the AI algorithm training.

Figure 1:
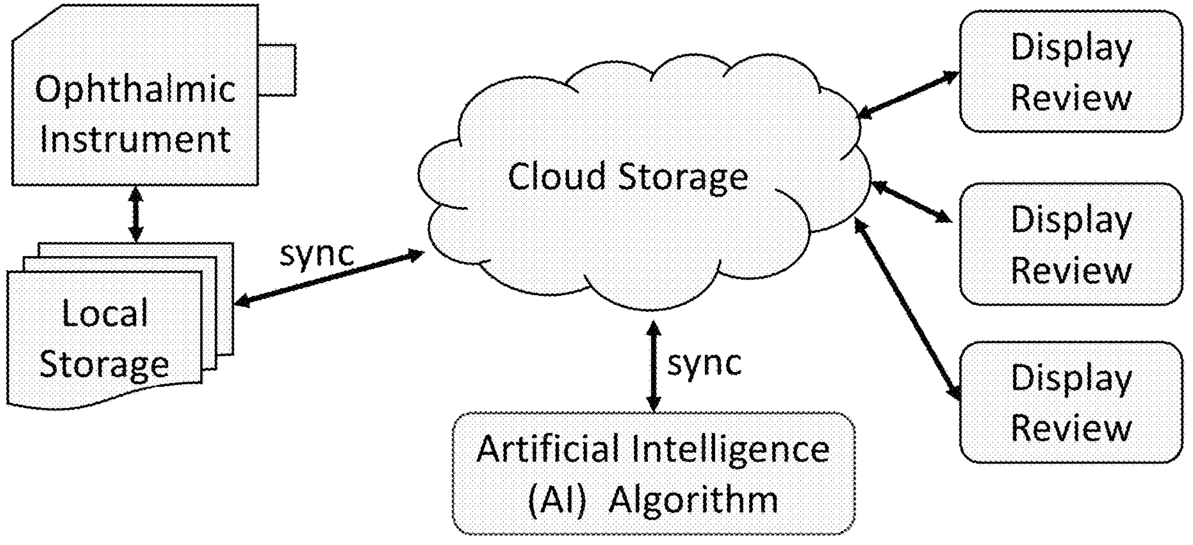
FIG. 1 show a flow chart of a first example illustrating generalized architecture and steps for data storage and transfer for an ophthalmic instrument, according to the present invention.

FIG. 1 depicts a flow chart of a first example illustrating generalized architecture and steps for data storage and transfer for an ophthalmic instrument, according to the present invention. Data is acquired by the instrument and is stored on local media. This data may consist of movies of aberrometry, images, corneal topography or other processed data. The acquired data is stored along with conditions of the measurement (target correction and fixation, illumination levels, etc).

After the measurement sequence is acquired, it is synchronized to a cloud storage system. This can either be a local intranet system with a dedicated server, or an Electronic Medical Records (EMR) system, or one of the many common cloud storage platforms (OneDrive, Google drive, Dropbox, etc). Preferably this data is secured with encryption that is medical device data compliant. Once the data is synchronized to the cloud-based storage, it can be viewed and analyzed by any number of separate data viewer/analysis programs. In addition, this data is available to the AI system, which is also cloud based. There are several pre-existing AI platforms, including Google AI Platform, Microsoft Azure, and Amazon AWS Machine Learning. There are other AI systems that may be built on local platforms, either with native or through the use of a standard platform (e.g., MATLAB).

Figure 2:
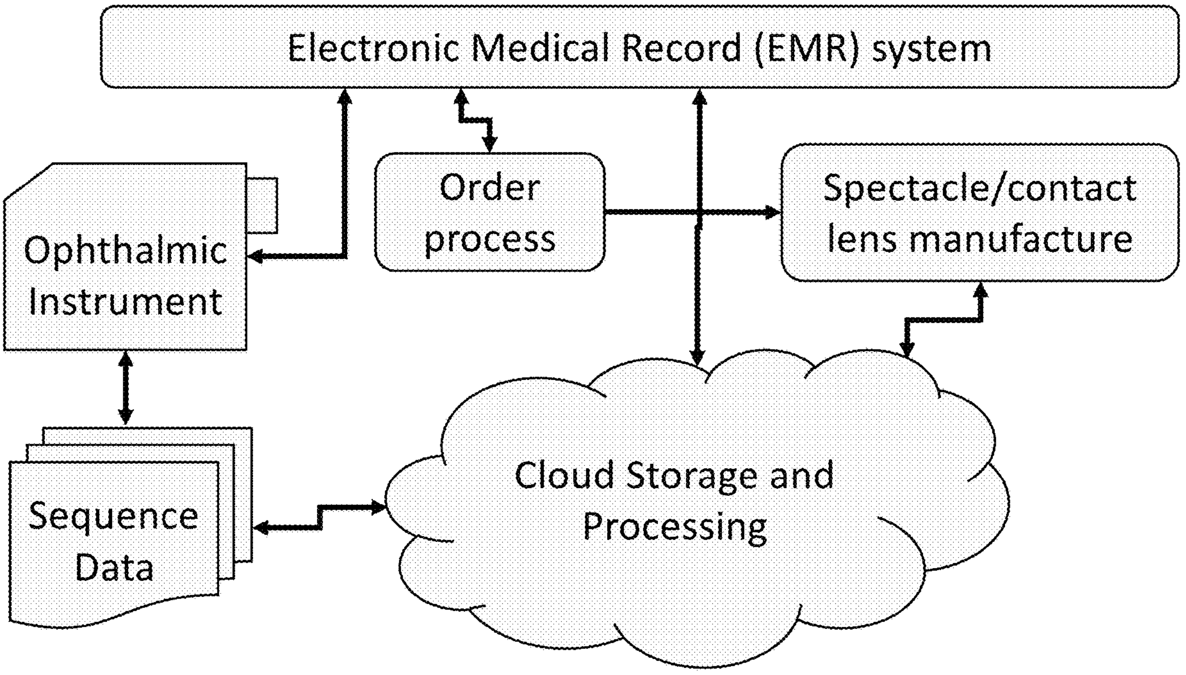
FIG. 2 shows a flow chart of a second example illustrating more detail on the cloud-based architecture data collection, according to the present invention.

FIG. 2 shows a flow chart of a second example illustrating more detail on the cloud-based architecture data collection, according to the present invention. As the measurement system is used to measure patients, some of this data is used by the eye care provider (ECP) to prescribe a prescription. This may be a refraction used for spectacles or contact lenses, or it may be more detailed, including: CL base curve, astigmatism, axis, higher order aberrations, or other features. This data is sent to the contact lens manufacturing laboratory using an order process which records the desired order parameters. Typically, the doctor uses an EMR system to track patient records. This will also record various outcome measures, including fit success and visual acuity (VA). This combination of order record with outcome success can be fed to the AI algorithm to provide training datasets.

Figure 3:
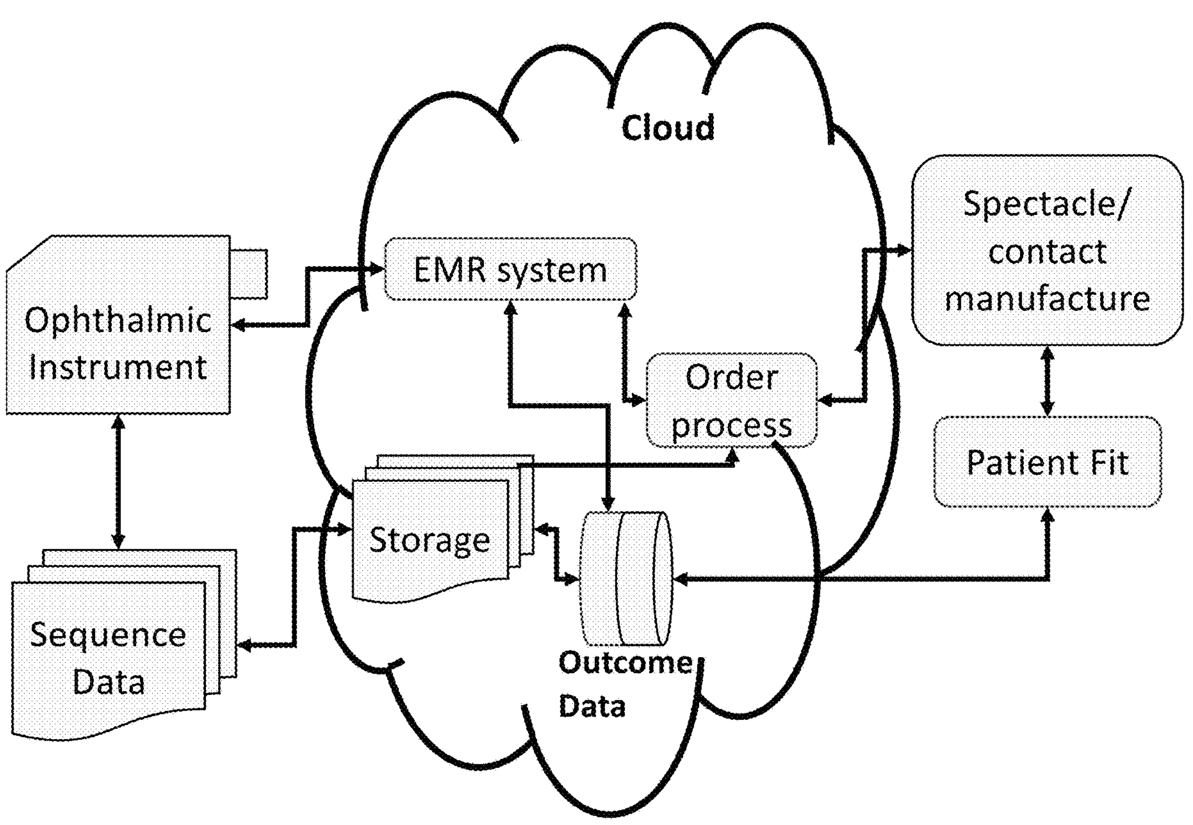
FIG. 3 shows a flow chart of a third example illustrating an alternative arrangement where more of the data collection features are cloud-based, according to the present invention.

FIG. 3 shows a flow chart of a third example illustrating an alternative embodiment where more of the data collection features are cloud-based, according to the present invention. Most EMR systems are now cloud-based to provide portability across platforms. Thus, the patient information, outcome measures, prescription history are already available in the cloud. The order process can also be cloud-based. The operations that take place outside the cloud are all physical interactions with the patient or correction (measuring the patient, manufacturing the contact lens or spectacles, and test fitting the correction on the patient). These can also be monitored with systems that could provide information to the cloud-based storage (re-measuring the patient plus correction with the ophthalmic instrument and/or correction metrology with cloud storage-linked equipment). The more the data collection can be automated, the more data will be available to the AI system.

Figure 4:
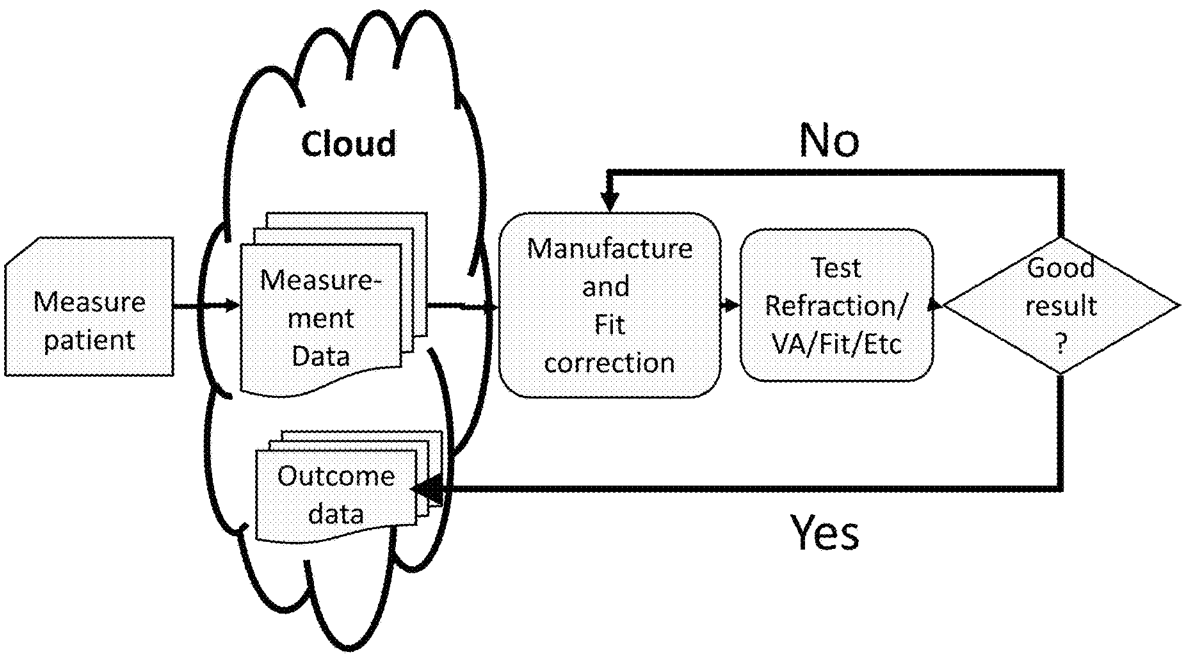
FIG. 4 shows a flow chart of a fourth example illustrating depicts that steps that are typical in a measurement/fitting cycle, according to the present invention.

FIG. 4 shows a flow chart of a fourth example illustrating depicts that steps that are typical in a measurement/fitting cycle, according to the present invention. The patient is measured with an ophthalmic device, which transmits its data to cloud-based storage (as described above). The appropriate contact lens is manufactured and then test-fit on the patient. The initial treatment design methodology can be anything that is familiar to the Eye Care Practitioner (ECP). The correction is then tested on the patient with any number of methods. This might be a slit lamp exam for contact lens fitting, or another measurement on the ophthalmic instrument. Outcome measures (lens comfort, visual acuity) may also be recorded (typically saved in the EMR). After test fitting, the ECP will make a decision about the correction. Either it doesn't work well enough, or it is acceptable and correct. It is important to record both of these outcomes so that the AI system will have both positive (success) and negative (poor outcome) measures to collect. The algorithm "learns" by correlating the score (outcomes) with the measurement data to provide an optimized treatment correction.

This methodology can be applied to several different ophthalmic corrections. This can include soft contact lenses, hard contact lenses, scleral lenses, spectacles, phakic, or pseudo-phakic Intraocular Lens (IOL), refractive surgery, cataract surgery, or LIRIC treatment. Improved measurement of the eye in a known state, and measurement of accommodative range, will provide improvements for presbyopia treatment, as well.

We claim:

1. A method for optimizing an ophthalmic treatment of a patient's eye, comprising:

a. measuring a patient's eye with an ophthalmic measurement instrument;

b. choosing a trial correction contact lens and measuring the patient's eye using the trial correction contact lens fitted on the eye;

c. determining a success criteria score for the trial correction contact lens;

d. using the success criteria score to provide training information to a machine-learning algorithm; and e. using the machine-learning algorithm to determine an optimal ophthalmic correction;

wherein the success criteria score is selected from the group consisting of fit, lens stability, and level of correction, or combinations thereof.

2. The method of claim 1 where the ophthalmic instrument comprises a wavefront aberrometer, a corneal topographer, a profilometer, a tomographer, or combinations of these instruments.

3. The method of claim 1, wherein measurement information is recorded dynamically as a function of time.

4. The method of claim 1, wherein a fixation condition of the eye is controlled through active stimulus with astigmatism and defocus correction.

5. The method of claim 4, wherein target defocus is dynamically controlled.

6. The method of claim 2, wherein measurement information is synchronized with cloud-based storage to provide a central storage location.

7. The method of claim 1, wherein outcome information is recorded through a cloud-based order process.

8. The method of claim 1, wherein the scoring information is recorded with an electronic medical records system.

9. The method of claim 1, wherein the ophthalmic correction comprises a soft contact lens.

10. The method of claim 1 wherein the ophthalmic correction comprises spectacle lenses.

11. The method of claim 1, wherein the ophthalmic correction comprises a gas permeable contact lens.

12. The method of claim 11, wherein the contact lens comprises a scleral contact lens.

13. The method of claim 1, wherein the ophthalmic correction comprises a result of laser refractive surgery.

14. The method of claim 1, wherein the ophthalmic correction comprises a phakic-IOL.

15. The method of claim 1, wherein the ophthalmic correction comprises a pseudo-phakic IOL.

16. The method of claim 14, further comprising using laser-induced refractive index change (LIRIC) for either multifocal correction or higher order aberration correction.

17. The method of claim 1, wherein the ophthalmic correction is implemented by changing an index of refraction of a native eye tissue.

18. A method for optimizing an ophthalmic treatment of a patient's eye, comprising:

a. measuring a patient's eye with a wavefront aberrometer;

b. choosing a trial correction contact lens and measuring the patient's eye using the trial correction contact lens fitted on the eye;

c. determining a success criteria score for the trial correction contact lens;

d. using the success criteria score to provide training information to a machine-learning algorithm; and e. using the machine-learning algorithm to determine an optimal ophthalmic correction;

wherein the success criteria score is selected from the group consisting of fit, lens stability, and level of correction, or combinations thereof.

19. A method for optimizing an ophthalmic treatment of a patient's eye, comprising:

a. measuring a patient's eye with a wavefront aberrometer;

b. choosing a trial correction contact lens and measuring the patient's eye using the trial correction contact lens fitted on the eye;

c. determining a success criteria score for the trial correction contact lens;

d. using the success criteria score to provide training information to a machine-learning algorithm; and e. using the machine-learning algorithm to determine an optimal ophthalmic correction;

f. wherein measurement information from the wavefront aberrometer is synchronized with cloud-based or network-based storage to provide a central storage location;

wherein the success criteria score is selected from the group consisting of fit, lens stability, and level of correction, or combinations thereof.

* * * * *